United States Patent
Stamford et al.

(10) Patent No.: US 7,157,472 B2
(45) Date of Patent: Jan. 2, 2007

(54) NEUROPEPTIDE Y Y5 RECEPTOR ANTAGONISTS

(75) Inventors: Andrew W. Stamford, Chatham Township, NJ (US); Yusheng Wu, New York, NY (US)

(73) Assignee: Schering Corporation, Kenilworth, NJ (US)

( * ) Notice: Subject to any disclaimer, the term of this patent is extended or adjusted under 35 U.S.C. 154(b) by 187 days.

(21) Appl. No.: 10/609,638

(22) Filed: Jun. 30, 2003

(65) Prior Publication Data

US 2004/0034008 A1    Feb. 19, 2004

Related U.S. Application Data

(60) Provisional application No. 60/393,327, filed on Jul. 2, 2002.

(51) Int. Cl.
*A61K 31/454* (2006.01)
*C07D 401/12* (2006.01)

(52) U.S. Cl. .................. 514/329; 546/211
(58) Field of Classification Search ........... 514/329; 546/211
See application file for complete search history.

(56) References Cited

U.S. PATENT DOCUMENTS

| | | | |
|---|---|---|---|
| 4,405,644 A | 9/1983 | Kabbe et al. | |
| 4,532,248 A | 7/1985 | Franckowiak et al. | |
| 4,616,014 A | 10/1986 | Teraji et al. | |
| 4,623,662 A | 11/1986 | De Vries | |
| 4,766,213 A | 8/1988 | Juraszyk et al. | |
| 4,895,841 A | 1/1990 | Sugimoto et al. | |
| 5,225,414 A | 7/1993 | Henning et al. | |
| 2005/0049237 A1* | 3/2005 | Atkinson et al. | 514/210.2 |

FOREIGN PATENT DOCUMENTS

| | | |
|---|---|---|
| EP | 0945439 A1 | 9/1999 |
| EP | 0955923 A1 | 11/1999 |
| GB | 2216890 | 10/1989 |
| JP | 08041006 | 2/1996 |
| WO | WO 8909212 | 10/1989 |
| WO | WO 9009801 | 9/1990 |
| WO | WO 96/16542 | 6/1996 |
| WO | WO 9730045 | 8/1997 |
| WO | WO 9853814 | 12/1998 |
| WO | WO 00/27845 | 5/2000 |
| WO | WO 0069849 | 11/2000 |
| WO | WO 0249648 | 6/2002 |
| WO | WO 03037274 | 5/2003 |

OTHER PUBLICATIONS

Chang, L et al. Substituted Imidazoles as Glucagon Receptor Antagonist, Bioorg. and Med. Chem. Letters, 2001, 11, pp. 2549-2553.*
International Search Report for PCT/US 03/20489 (CN01595K), dated Jun. 3, 2003—5 Pages.
Stanley, et al. "Neuropeptide Y injected in the paraventicular hypothalamus: A powerful stimulant of feeding behavior" *Proc. Natl. Acad. Sci.* 82:3940-3943(1985).
Billington, et al. "Effects of intracerebroventricular injection of neuropeptide Y on energy metabolism" *Am. J. Physiol.* 260:R321-R327 (1991).
Wahlestedt, et al. "Neuropeptide Y-related peptides and their receptors—are the receptors potential therapeutic drug targets?" *Annu. Rev. Pharmacol. Toxicol.* 32:309-352(1993).
Gerald, et al. "A receptor subtype involved in neuropeptide-Y-induced food intake" *Nature* 382:168-171 (1996).
Gehlert, D., "Minireview—Multiple Receptors for the Pancreatic Polypeptide (PP-Fold) Family: Physiological Implications" *Proc. Soc. Exp. Biol. Med.* 218:7-22(1998).
Michel, et al., "XVI. International Union of Pharmacology Recommendations for the Nomenclature of Neuropeptide Y, Peptide YY, and Pancreatic Polypeptide Receptors" *Pharmacol. Rev.* 50(1):143-150(1998).
Hwa, et al. "Activation of the NPY Y5 receptor regulates both feeding and energy expenditure" *American J. Physiological* 277(46):R1428-R1434(1999).

* cited by examiner

*Primary Examiner*—Kamal A. Saeed
*Assistant Examiner*—Nyeemah Grazier
(74) *Attorney, Agent, or Firm*—William Y. Lee

(57) ABSTRACT

The present invention discloses compounds which, are receptor antagonists for NPY Y5 as well as methods for preparing such compounds. In another embodiment, the invention discloses pharmaceutical compositions comprising such NPY Y5 receptor antagonists as well as methods of using them to treat obesity, metabolic disorders, eating disorders such as hyperphagia, and diabetes.

15 Claims, No Drawings

NEUROPEPTIDE Y Y5 RECEPTOR ANTAGONISTS

CROSS REFERENCE TO RELATED APPLICATIONS

This application claims the benefit of U.S. Provisional Application No. 60/393,327 filed on Jul. 2, 2002.

FIELD OF THE INVENTION

The present invention relates to neuropeptide Y Y5 receptor antagonists useful in the treatment of metabolic and eating disorders, pharmaceutical compositions containing the compounds, and methods of treatment using the compounds.

BACKGROUND OF THE INVENTION

Neuropeptide Y (NPY) is a 36 amino acid neuropeptide that is widely distributed in the central and peripheral nervous systems. NPY is a member of the pancreatic polypeptide family that also includes peptide YY and pancreatic polypeptide (Wahlestedt, C., and Reis, D., Ann. Rev. Toxicol., 32, 309, 1993). NPY elicits its physiological effects by activation of at least six receptor subtypes designated Y1, Y2, Y3, Y4, Y5 and Y6 (Gehlert, D., Proc. Soc. Exp. Biol. Med., 218, 7, 1998; Michel, M. et al., Pharmacol. Rev., 50, 143, 1998). Central administration of NPY to animals causes dramatically increased food intake and decreased energy expenditure (Stanley, B. and Leibowitz, S., Proc. Natl. Acad. Sci. USA 82: 3940, 1985; Billington et al., Am J. Physiol., 260, R321, 1991). These effects are believed to be mediated at least in part by activation of the NPY Y5 receptor subtype. The isolation and characterization of the NPY Y5 receptor subtype has been reported (Gerald, C. et al., Nature, 1996, 382, 168; Gerald, C. et al. WO 96/16542). Additionally, it has been reported that activation of the NPY Y5 receptor by administration of the Y5—selective agonist [D-Trp$^{32}$]NPY to rats stimulates feeding and decreases energy expenditure (Gerald, C. et al., Nature, 1996, 382, 168; Hwa, J. et al., Am. J. Physiol., 277 (46), R1428, 1999).

PCT patent application WO 00/27845 describes a class of compounds, characterized therein as spiro-indolines, said to be selective neuropeptide Y Y5 receptor antagonists and useful for the treatment of obesity and the complications associated therewith. Urea derivatives indicated as possessing therapeutic activity are described in U.S. Pat. Nos. 4,623,662 (antiatherosclerotic agents) and 4,405,644 (treatment of lipometabolism).

Provisional application, U.S. Ser. No. 60/232,255 describes a class of substituted urea neuropeptide Y Y5 receptor antagonists.

SUMMARY OF THE INVENTION

In one embodiment, this invention provides novel compounds having NPY Y5 receptor antagonist activity. These compounds are represented by structural formula I:

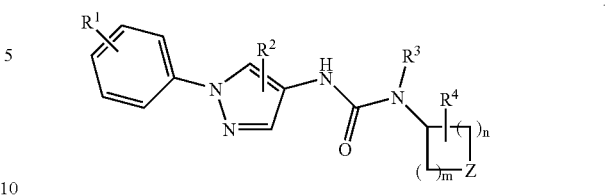

or a pharmaceutically acceptable salt or solvate, wherein:
m is a number from 1 to 3;
n is a number from 1 to 3;
m and n maybe the same or different;
$R^1$ is 0 to 5 substituents which can be the same or different, each being independently, —OH, halogen, alkyl, haloalkyl, cycloalkyl, —CN, alkoxy, cycloalkoxy, alkylthio-, cycloalkylthio-, —NR$^5$R$^6$, —NO$_2$, —C(O)NR$^5$R$^6$, —NR$^5$C(O)R$^6$, —NR$^5$C(O)NR$^5$R$^6$ where the two R$^5$ moieties can be the same or different, —NC(O)OR$^7$, —C(O)OR$^5$, —SOR$^5$, —SO$_2$R$^5$, —SO$_2$NR$^5$R$^6$, aryl or heteroaryl;
$R^2$ is 0 to 2 subsitutuents which can be the same or different, each being independently, —OH, halogen, alkyl, haloalkyl, cycloalkyl, —CN, alkoxy, cycloalkoxy, alkylthio-, cycloalkylthio-, —NR$^5$R$^6$, —NO$_2$, —C(O)NR$^5$R$^6$, —NR$^5$C(O)R$^6$, —NR$^5$C where the two R$^5$ moieties can be the same or different, —NC(O)OR$^7$, —C(O)OR$^5$, —SOR$^5$, —SO$_2$R$^5$, —SO$_2$NR$^5$R$^6$, aryl or heteroaryl;
$R^3$ is hydrogen or alkyl;
$R^4$ is 0 to 6 substituents which can be the same or different, each being independently alkyl, alkoxy, heteroaryl, aralkyl-, heteroaralkyl-, haloalkyl or —OH;
$R^5$ and $R^6$ can be the same or different each being independently hydrogen, alkyl, aryl, heteroaryl, aralkyl, heteroaralkyl, haloalkyl or cycloalkyl;
$R^7$ is alkyl or cycloalkyl;
Z is NR$^8$ or CR$^3$R$^9$;
$R^8$ is hydrogen, alkyl, cycloalkyl, alkyl substituted with a cycloalkyl group, aryl, heteroaryl, aralkyl-, heteroaralkyl-, —SO$_2$R$^{10}$, —SO$_2$NR$^5$R$^{11}$, —C(O)R$^{11}$, —C(O)NR$^5$R$^{—C(O)OR^{10}}$;
$R^9$ is hydrogen, alkyl, —OH, alkoxy, —NR$^5$R$^{11}$, aryl, or heteroaryl; or $R^3$ and $R^9$ can be joined together and with the carbon to which they are attached form a 3 to 7-membered ring;
$R^{10}$ is alkyl, cycloalkyl, aryl or heteroaryl; and
$R^{11}$ is hydrogen, alkyl, cycloalkyl, aryl or heteroaryl.

This invention is also directed to pharmaceutical compositions for the treatment of metabolic disorders such as obesity, and eating disorders such as hyperphagia. In one aspect, this invention is also directed to pharmaceutical compositions for the treatment of obesity which comprise an obesity treating amount of a compound of formula I, or a pharmaceutically acceptable salt or solvate of said compound, and a pharmaceutically acceptable carrier.

DETAILED DESCRIPTION

The present invention relates to compounds represented by structural formula I, or a pharmaceutically acceptable salt or solvate thereof, wherein the various moieties are as described above.

The compounds of formula I can be administered as racemic mixtures or enantiomerically pure compounds.

A preferred group of compounds are compounds of formula I wherein $R^1$ is a halogen.

A further preferred group of compounds of formula I are those in which $R^1$ is 2 substituents, each of which is fluorine.

Another group of preferred compounds are compounds of formula I wherein $R^2$ is 2 substituents.

Another preferred group of compounds are compounds in which $R^2$ is zero.

Another preferred group of compounds are compounds of formula I wherein $R^3$ is alkyl.

Another preferred group of compounds are compounds in which $R^3$ is methyl.

Another preferred group of compounds are compounds of formula I wherein m is 2 and n is 2, $R^4$ is hydrogen and Z is $NR^8$.

Another preferred group of compounds are compounds of formula I wherein $R^8$ is —$SO_2CH_3$, —$C(O)OC(CH_3)_3$, hydrogen, —$C(O)CH_3$, —$C(O)CH_2CH_3$, —$C(O)$cyclopropyl, —$C(O)CH(CH_3)_2$, —$SO_2CH_2CH_3$ or —$SO_2CH(CH3)_2$.

Another group of preferred compounds are compounds of formula II

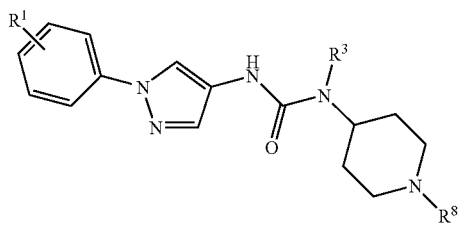

formula II or a pharmaceutically acceptable salt or solvate thereof, wherein:

$R^1$ is 2 substituents which are halogens that can be the same or different;

$R^3$ is alkyl; and $R^8$ is —$SO_2R^{10}$ or —$C(O)R^{11}$.

A set of preferred compounds are listed below in Table 1.

Compounds of formula I can be useful as highly selective, high affinity NPY Y5 receptor antagonists useful for the treatment of obesity.

Except where stated otherwise, the following definitions apply throughout the present specification and claims. These definitions apply regardless of whether a term is used by itself or in combination with other terms. Hence the definition of "alkyl" applies to "alkyl" as well as to the "alkyl" portions of "alkoxy", "alkylamino" etc.

As used above, and throughout the specification, the following terms, unless otherwise indicated, shall be understood to have the following meanings:

"Patient" includes both human and animals.

"Mammal" means humans and other mammalian animals.

"Alkyl" means an aliphatic hydrocarbon group, which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means an alkyl group having about 1 to about 6 carbon atoms in the chain, which may be straight or branched. The term "substituted alkyl" means that the alkyl group may be substituted by one or more substituents which may be the same or different, each substituent being independently selected from the group consisting of halo, alkyl, aryl, -cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl, n-butyl, and t-butyl.

"Alkenyl" means an aliphatic hydrocarbon group comprising at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means an alkenyl group having about 2 to about 6 carbon atoms in the chain, which may be straight or branched. The term "substituted alkenyl" means that the alkenyl group may be substituted by one or more substituents which may be the same or different, each substituent being independently selected from the group consisting of halo, alkyl, aryl, -cycloalkyl, cyano, and alkoxy. Non-limiting examples of suitable alkenyl groups include ethenyl, propenyl, n-butenyl, and 3-methylbut-2-enyl.

"Alkynyl" means an aliphatic hydrocarbon group comprising at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means an alkynyl group having about 2 to about 6 carbon atoms in the chain, which may be straight or branched. Non-limiting examples of suitable alkynyl groups include ethynyl, propynyl and 2-butynyl. The term "substituted alkynyl" means that the alkynyl group may be substituted by one or more substituents which may be the same or different, each substituent being independently selected from the group consisting of alkyl, aryl and -cycloalkyl.

"Aryl" means an aromatic monocyclic or multicyclic ring system comprising about 6 to about 14 carbon atoms, preferably about 6 to about 10 carbon atoms. The aryl group can be unsubstituted or substituted on the ring with one or more substituents which may be the same or different, each being independently selected from the group consisting of alkyl, aryl, $OCF_3$, OCOalkyl, OCOaryl, $CF_3$, heteroaryl, aralkyl, alkylaryl, heteroaralkyl, alkylheteroaryl, hydroxy, hydroxyalkyl, alkoxy, aryloxy, aralkoxy, acyl, aroyl, halo, haloalkyl, haloalkoxy, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, -cycloalkyl and heterocyclyl. Non-limiting examples of suitable aryl groups include phenyl and naphthyl. The "aryl" group can also be substituted by linking two adjacent carbons on its aromatic ring via a combination of one or more carbon atoms and one or more oxygen atoms such as, for example, methylenedioxy, ethylenedioxy, and the like.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, -cycloalkyl, cycloalkenyl and heterocyclyl. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrrolyl, triazolyl, and the like.

"Aralkyl" means an aryl-alkyl-group in which the aryl and alkyl are as previously described. Preferred aralkyls comprise a lower alkyl group. Non-limiting examples of suitable aralkyl groups include benzyl, 2-phenethyl and a naphthlenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl groups is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl and heterocyclyl. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Halo" means fluoro, chloro, bromo or iodo groups. Preferred are fluoro, chloro or bromo, and more preferred are fluoro and chloro.

"Halogen" means fluorine, chlorine, bromine or iodine. Preferred are fluorine, chlorine or bromine, and more preferred are fluorine and chlorine.

"Haloalkyl" means an alkyl as defined above wherein one or more hydrogen atoms on the alkyl is replaced by a halo group defined above.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl and heterocyclyl. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl and heterocyclyl. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, pyranyl, tetrahydrothiophenyl, morpholinyl and the like.

"Aralkenyl" means an aryl-alkenyl-group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-3-ylmethyl. The bond to the parent moiety is through the alkyl.

"Heteroaralkenyl" means an heteroaryl-alkenyl-group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)—, alkenyl-C(O)—, Alkynyl-C(O)—, cycloalkyl-C(O)—, cycloalkenyl-C(O)—, or cycloalkynyl-C(O)— group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, and cyclohexanoyl.

"Aroyl" means an aryl-C(O)— group in which the aryl group is as previously described. The bond to the parent moiety is through the carbonyl. Non-limiting examples of suitable groups include benzoyl and 1- and 2-naphthoyl.

"Alkoxy" means an alkyl-O— group in which the alkyl group is as previously described. Non-limiting examples of suitable alkoxy groups include methoxy, ethoxy, n-propoxy and isopropoxy. The alkyl group is linked to an adjacent moiety through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Alkylthio" means an alkyl-S— group in which the alkyl group is as previously described. Non-limiting examples of suitable alkylthio groups include methylthio, ethylthio, i-propylthio and heptylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkoxy group defined earlier linked to an adjacent moiety through a carbonyl. Non-limiting examples of alkoxycarbonyl groups include —C(O)—CH$_3$, —C(O)—CH$_2$CH$_3$ and the like.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Alkylsulfinyl" means an alkyl-S(O)— group. Preferred groups are those in which the alkyl group is lower alkyl. The bond to the parent moiety is through the sulfinyl.

"Arylsulfonyl" means an aryl-S(O$_2$)— group. The bond to the parent moiety is through the sulfonyl. "Arylsulfinyl" means an aryl-S(O)— group. The bond to the parent moiety is through the sulfinyl.

The term "optionally substituted" means optional substitution with the specified groups, radicals or moieties.

As used herein, the term "composition" is intended to encompass a product comprising the specified ingredients in the specified amounts, as well as any product which results, directly or indirectly, from combination of the specified ingredients in the specified amounts.

Solvates of the compounds of the invention are also contemplated herein. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$O.

"Effective amount" or "therapeutically effective amount" is meant to describe an amount of compound of the present invention effective to treat a mammal (e.g., human) having a disease or condition mediated by YY5, and thus producing the desired therapeutic effect.

The compound of formula I forms salts which are also within the scope of this invention. Reference to a compound of formula I, herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compound of the formula I may be formed, for example, by reacting a compound of formula I with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulfonates, bisulfates, borated, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1)1–19; P. Gould, *International J. of Pharmaceutics* (1986) 33 201–217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of formula I, and salts and solvates thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts and solvates of the compounds), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" and the like, is intended to equally apply to the salt and solvate of enantiomers, stereoisomers, rotamers, tautomers or racemates of the inventive compounds.

Compounds of formula I, which can be useful as highly selective, high affinity NPY Y5 receptors antagonists, may be used in combination with other compounds including other "different" compounds that are also useful as NPY Y5 receptor antagonists. When the term "different" is used, it is intended that these other compounds are chemically different from the compounds of formula I.

When any variable (e.g., aryl, heterocycle, R², etc.) occurs more than one time in any constituent or in formula I, its definition on each occurrence is independent of its definition at every other occurrence. Also, combinations of substituents and/or variables are permissible only if such combinations result in stable compounds.

A preferred group of compounds are those listed below in Table I.

TABLE I

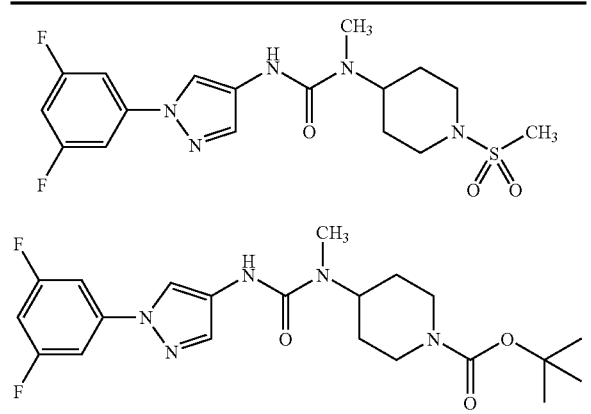

TABLE I-continued

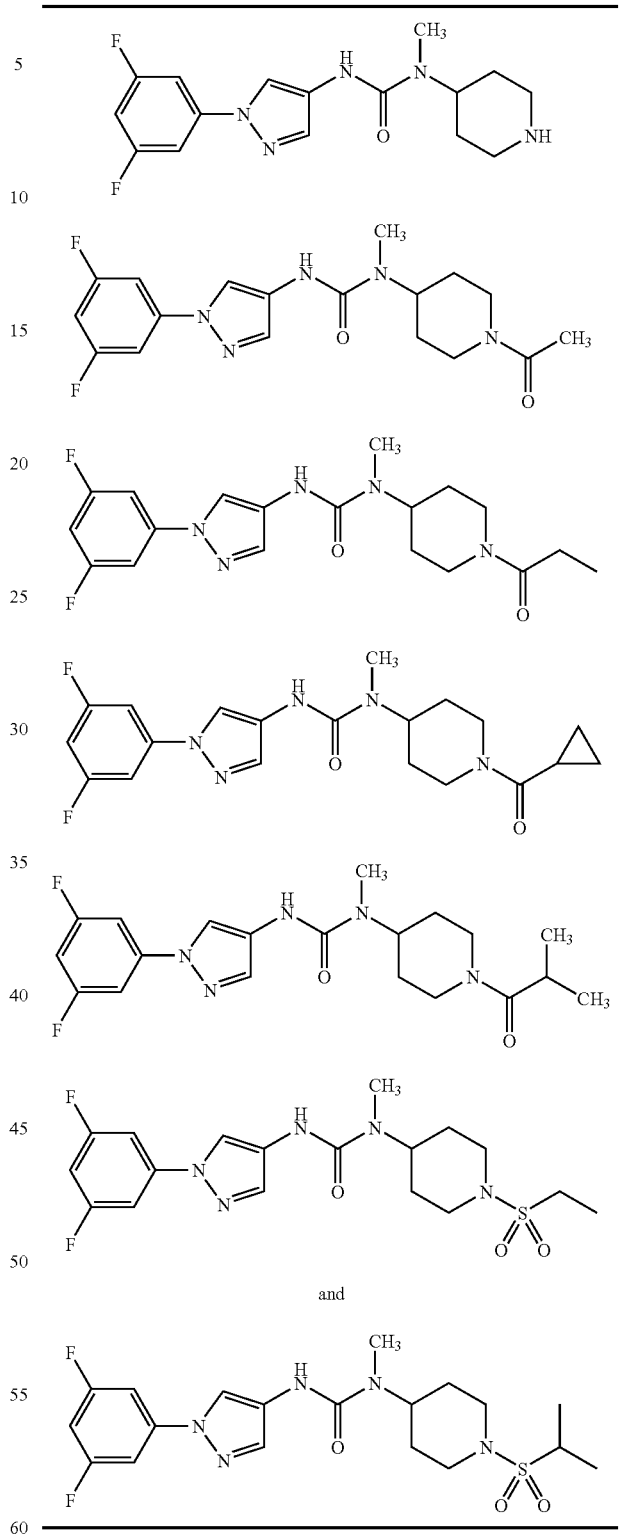

and as well as their pharmaceutically acceptable salts or solvates.

Another aspect of this invention is a method of treating a mammal (e.g., human) having a disease or condition mediated by NPY Y5 receptor antagonist by administering a therapeutically effective amount of at least one compound of formula I, or a pharmaceutically acceptable salt or solvate of said compound to the mammal.

A useful dosage is about 0.001 to 100 mg/kg of body weight/day of the compound of formula I. A preferred dosage is about 0.01 to 25 mg/kg of body weight/day of a compound of formula I, or a pharmaceutically acceptable salt or solvate of said compound.

Another aspect of this invention is directed to a method of treating obesity comprising administering to a mammal in need of such treatment a therapeutically effective amount of at least one compound of formula I, or a pharmaceutically acceptable salt or solvate of said compound.

Another aspect of this invention is directed to a method for treating eating and metabolic disorders such as bulimia and anorexia comprising administering to a mammal a therapeutically effective amount of at least one compound of formula I, or a pharmaceutically acceptable salt or solvate of said compound.

Another aspect of this invention is directed to a method for treating hyperlipidemia comprising administering to a mammal a therapeutically effective amount of at least one compound of formula I, or a pharmaceutically acceptable salt or solvate of said compound.

Another aspect of this invention is directed to a method for treating cellulite and fat accumulation comprising administering to a mammal a therapeutically effective amount of at least one compound of formula I, or a pharmaceutically acceptable salt or solvate of said compound.

Another aspect of this invention is directed to a method for treating type II diabetes comprising administering to a mammal a therapeutically effective amount of at least one compound of formula I, or a pharmaceutically acceptable salt or solvate of said compound.

In addition to the "direct" effect of the compounds of this invention on the NPY Y5 receptor, there are diseases and conditions that can benefit from the weight loss such as insulin resistance, impaired glucose tolerance, Type II Diabetes, hypertension, hyperlipidemia, cardiovascular disease, gall stones, certain cancers, and sleep apnea.

This invention is also directed to pharmaceutical compositions which comprise at least one compound of formula I, or a pharmaceutically acceptable salt or solvate of said compound and at least one pharmaceutically acceptable carrier.

This invention is also directed to pharmaceutical compositions for the treatment of obesity which comprise an obesity treating amount of at least one compound of formula I, or a pharmaceutically acceptable salt or solvate of said compound and at least one pharmaceutically acceptable carrier.

Compounds of formula I, can be produced by processes known to those skilled in the art using either solution phase or solid phase synthesis as shown in the following reaction schemes, in the preparations and examples below.

Compounds of formula I can be prepared by Scheme 1, as follows:

Scheme 1

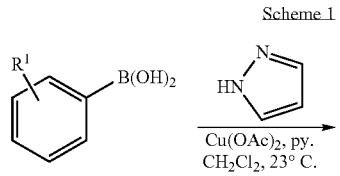

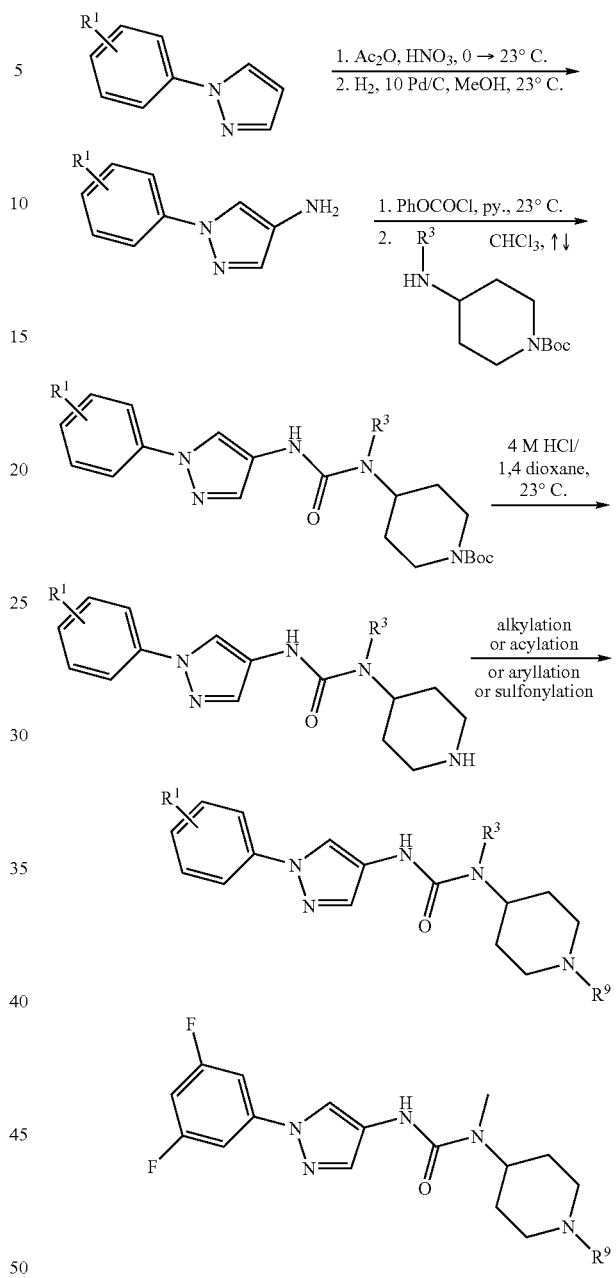

Compounds of formula I (wherein $R^8$ is $SO_2Me$) can be prepared by Scheme 2.

Scheme 2

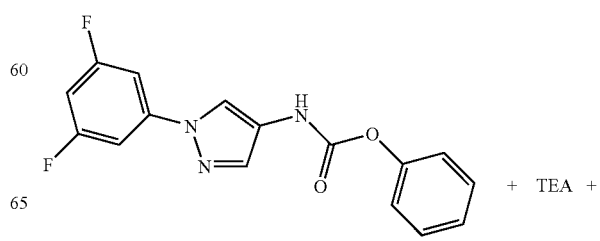

-continued

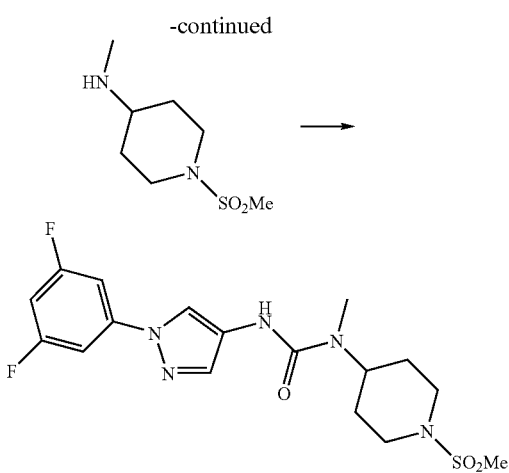

Combinatorial libraries of compounds of formula I can also be prepared using solid phase chemistry as shown in the schemes above.

Alternative mechanistic pathways and analogous structures within the scope of the invention would be apparent to those skilled in the art.

Starting materials are prepared by known methods and/or methods described in the Preparations.

The compounds of formula I can exhibit NPY Y5 receptor antagonizing activity, which has been correlated with pharmaceutical activity for treating eating disorders, such as obesity and hyperphagia, and diabetes.

The compounds of formula I display pharmacological activity in a test procedure designed to demonstrate NPY Y5 receptor antagonist activity. The compounds are non-toxic at pharmaceutically therapeutic doses.

cAMP Assay

HEK-293 cells expressing the Y5 receptor subtype were maintained in Dulbecco's modified Eagles' media (Gico-BRL) supplemented with 10% FCS (ICN), 1% penicillin-streptomycin and 200 μg/ml Geneticin®(GibcoBRL #11811-031) under a humidified 5% $CO_2$ atmosphere. Two days prior to assay, cells were released from T-175 tissue culture flasks using cell dissociation solution (1×; non-enzymatic [Sigma #C-5914]) and seeded into 96-well, flat-bottom tissue culture plates at a density of 15,000 to 20,000 cells per well. After approximately 48 hours, the cell monolayers were rinsed with Hank's balanced salt solution (HBSS) then preincubated with approximately 150 μl/well of assay buffer (HBSS supplemented with 4 mM $MgCl_2$, 10 mM HEPES, 0.2% BSA [HH]) containing 1 mM 3-isobutyl-1-methylxanthine ([IBMX] Sigma #I-587) with or without the antagonist compound of interest at 37° C. After 20 minutes the 1 mM IBMX-HH assay buffer (± antagonist compound) was removed and replaced with assay buffer containing 1.5 μM (CHO cells) or 5 μM (HEK-293 cells) forskolin (Sigma #F-6886) and various concentrations of NPY in the presence or absence of one concentration of the antagonist compound of interest. At the end of 10 minutes, the media were removed and the cell monolayers treated with 75 μl ethanol. The tissue culture plates were agitated on a platform shaker for 15 minutes, after which the plates were transferred to a warm bath in order to evaporate the ethanol. Upon bringing all wells to dryness, the cell residues were resolubilized with 250 μl FlashPlate® assay buffer. The amount of cAMP in each well was quantified using the [$^{125}$I]-cAMP FlashPlate® kit (NEN #SMP-001) and according to the protocol provided by the manufacturer. Data were expressed as either pmol cAMP/ml or as percent of control. All data points were determined in triplicate and $EC_{50}$'s (nM) were calculated using a nonlinear (sigmoidal) regression equation (GraphPad Prism™). The $K_B$ of the antagonist compound was estimated using the following formula:

$$K_B=[B]/(1-\{[A']/[A]\})$$

where

[A] is the $EC_{50}$ of the agonist (NPY) in the absence of antagonist,

[A'] is the $EC_{50}$ of the agonist (NPY) in the presence of antagonist, and

[B] is the concentration of the antagonist.

NPY Receptor Binding Assay

Human NPY Y5 receptors were expressed in CHO cells. Binding assays were performed in 50 mM HEPES, pH 7.2, 2.5 mM $CaCl_2$, 1 mM $MgCl_2$ and 0.1% BSA containing 5–10 μg of membrane protein and 0.1 nM $^{125}$L-peptide YY in a total volume of 200 μl. Non-specific binding was determined in the presence of 1 μM NPY. The reaction mixtures were incubated for 90 minutes at room temperature then filtered through Millipore MAFC glass fiber filter plates which had been pre-soaked in 0.5% polyethleneimine. The filters were washed with phosphate-buffered saline, and radioactivity was measured in a Packard TopCount scintillation counter.

For the compounds of this invention, a range of neuropeptide Y5 receptor binding activity from about 0.2 nM to about 500 nM was observed. Compounds of this invention preferably have a binding activity in the range of about 0.2 nM to 250 nM, more preferably about 0.2 to 100 nM, and most preferably about 0.2 to 10 nM.

Yet another aspect of this invention are combinations of a compound of Formula I or a pharmaceutically acceptable salt or solvate of said compound and other compounds as described below.

One such aspect of this invention is a method for treating obesity comprising administering to a mammal (e.g., a female or male human)

a. an amount of at least one first compound, said first compound being a Formula I compound or a pharmaceutically acceptable salt or solvate of said compound; and b. an amount of at least one second compound, said second compound being at lease one anti-obesity and/or anorectic agent such as a $\beta_3$ agonist, thyromimetic agent, anoretic agent, or NPY antagonist different from the first compound wherein the amounts of the first and second compounds result in a therapeutic effect.

Yet another aspect of this invention are combinations of a compound of formula I, or a pharmaceutically acceptable salt or solvate of said compound and other compounds as described below.

This invention is also directed to a pharmaceutical combination composition comprising: a therapeutically effective amount of a composition comprising at least one first compound, said first compound being a compound of formula I, or a pharmaceutically acceptable salt or solvate of said compound at least one second compound, said second compound being at least one antiobesity and/or anorectic agent such as a $\beta_3$ agonist, thyromimetic agent, anoretic, or an NPY antagonist different from the first compound; and/or optionally a pharmaceutical carrier, vehicle or diluent.

Another aspect of this invention is a kit comprising:

a. an amount of a compound of formula I, or a pharmaceutically acceptable salt or solvate of said compound and a pharmaceutically acceptable carrier, vehicle or diluent in a first unit dosage form;

b. an amount of an antiobesity and/or anorectic agent such as a $\beta_3$ agonist, thyromimetic agent, anoretic agent, or NPY antagonist different from the compound of formula I and a pharmaceutically acceptable carrier, vehicle or diluent in a second unit dosage form; and c. means for containing said first and second dosage forms wherein the amounts of the first and second compounds result in a therapeutic effect.

Preferred antiobesity and/or anorectic agents (taken singly or in any combination thereof) in the above combination methods, combination compositions and combination kits are:

phenylpropanolamine, ephedrine, pseudoephedrine, phentermine, a cholecystokinin-A (hereinafter referred to as CCK-A) agonist, a monoamine reuptake inhibitor (such as sibutramine), a sympathomimetic agent, a serotonergic agent (such as dexfenfluramine or fenfluramine), a dopamine agonist (such as bromocriptine), a melanocyte-stimulating hormone receptor agonist or mimetic, a melanocyte-stimulating hormone analog, a cannabinoid receptor antagonist, a melanin concentrating hormone antagonist, the OB protein (hereinafter referred to as "leptin"), a leptin analog, a leptin receptor agonist, a galanin antagonist or a GI lipase inhibitor or decreaser (such as orlistat). Other anorectic agents include bombesin agonists, dehydroepiandrosterone or analogs thereof, glucocorticoid receptor agonists and antagonists, orexin receptor antagonists, urocortin binding protein antagonists, agonists of the glucagon-like peptide-1 receptor such as Exendin and ciliary neurotrophic factors such as Axokine.

Another aspect of this invention is a method treating diabetes comprising administering to a mammal (e.g., a female or male human)

a. an amount of a first compound, said first compound being a compound of formula I, or a pharmaceutically acceptable salt or solvate of said compound; and b. an amount of a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone or GW-1929, a sulfonylurea, glipazide, glyburide, or chlorpropamide wherein the amounts of the first and second compounds result in a therapeutic effect.

This invention is also directed to a pharmaceutical combination composition comprising: a therapeutically effective amount of a composition comprising a first compound, said first compound being a compound of formula I, or a pharmaceutically acceptable salt or solvate of said compound;

a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide; and optionally a pharmaceutical carrier, vehicle or diluent.

Another aspect of this invention is a kit comprising:

a. an amount of a compound of formula I, or a pharmaceutically acceptable salt or solvate of said compound and a pharmaceutically acceptable carrier, vehicle or diluent in a first unit dosage form;

b. an amount of an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide and a pharmaceutically acceptable carrier, vehicle or diluent in a second unit dosage form; and c. means for containing said first and second dosage forms wherein the amounts of the first and second compounds result in a therapeutic effect.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent compound of formula i. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 1000 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 50 mg/day, in two to four divided doses.

The invention disclosed herein is exemplified by the following preparations and examples which should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% CH$_3$CN, 5 min—95% CH$_3$CN, 7 min—95% CH$_3$CN, 7.5 min—10% CH$_3$CN, 9 min—stop. The retention time and observed parent ion are given.

The following constituents, solvents and reagents may be referred to by their abbreviations in parenthesis:

TLC (thin-layer chromatography);
sodium triacetoxyborohydride (NaBH(OAc)$_3$);
THF (tetrahydrofuran);
DME (1,2-dimethoxyethane);
EtOAc (ethyl acetate);
Et$_3$N (triethylamine);
MeOH (methanol);
TEA (triethylamine)
CH$_3$NH$_2$ (methylamine);
CH$_3$CN (acetonitrile);
Na$_2$SO$_4$ (sodium sulfate);
NaHCO$_3$ (sodium bicarbonate);
CH$_2$Cl$_2$ (methylene dichloride)
and Boc (tert-butoxycarbonyl).

Experimental Details

Compounds of the invention have the following binding affinity at the human neuropeptide YY5 receptor subtype (hY5), NMR and Mass Spec.:

| MOLECULAR STRUCTURE Receptor Binding Activity | $^1$H NMR | MS (M + H) |
|---|---|---|
| 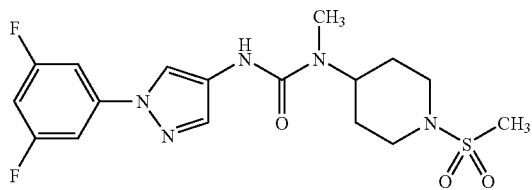<br>Y5 Ki = 2.4 nM | (CDCl$_3$) δ 8.29 (s, 1H), 7.62 (s, 1H), 7.23 (m, 2H), 6.68 (m, 1H), 6.36 (s, 1H), 4.42 (m, 1H), 3.92 (d, 2H), 2.90 (s, 3H), 2.79 (m, 5H), 1.80 (m, 4H). | 414 |
| 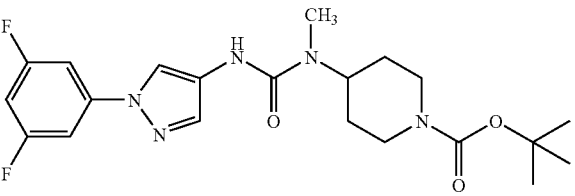<br>Y5 Ki = 1.8 nM | (CDCl$_3$) δ 8.32 (s, 1H), 7.60 (s, 1H), 7.25 (m, 2H), 6.68 (m, 1H), 6.30 (s, 1H), 4.42 (m, 1H), 4.25 (s, br, 2H), 2.87 (s, 3H), 2.81 (m, 2H), 1.62 (m, 4H), 1.50 (s, 9H). | 436 |
| 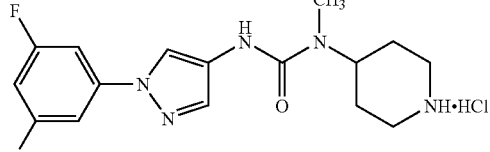<br>Y5 Ki = 276 nM | (CD$_3$OD) δ 8.31 (s, 1H), 7.77 (s, 1H), 7.39 (m, 2H), 6.85 (m, 1H), 4.43 (m, 1H), 3.50 (m, 2H), 3.18 (m, 2H), 2.94 (s, 3H), 2.18–1.90 (m, 4H). | 336 |

| MOLECULAR STRUCTURE<br>Receptor Binding Activity | $^1$H NMR | MS<br>(M + H) |
|---|---|---|
| 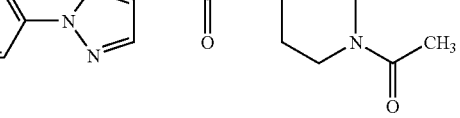<br>Y5 Ki = 1.6 nM | (CDCl$_3$) δ 8.30 (s, 1H),<br>7.60 (s, 1H), 7.21 (m, 2H),<br>6.67 (m, 1H), 6.54 (s, 1H),<br>4.76 (d, br, 1H), 4.50 (m, 1H),<br>3.90 (d, br, 1H), 3.19 (t, 1H),<br>2.86 (s, 3H),<br>2.62 (t, 1H), 2.12 (s, 3H),<br>1.90–1.50 (m, 4H). | 378 |
| 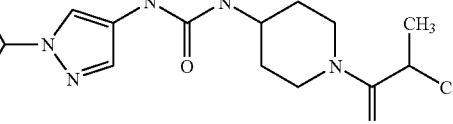<br>Y5 Ki = 0.96 nM | (CDCl$_3$) δ 8.31 (s, 1H),<br>7.60 (s, 1H), 7.22 (m, 2H),<br>6.68 (m, 1H), 6.42 (s, 1H),<br>4.78 (s, br, 1H), 4.50 (m, 1H),<br>3.95 (s, br, 1H), 3.15 (s, br, 1H),<br>2.86 (s, 3H), 2.65 (s, br, 1H),<br>2.37 (q, 2H), 1.90–1.50 (m, 4H),<br>1.16 (t, 3H). | 392 |
| 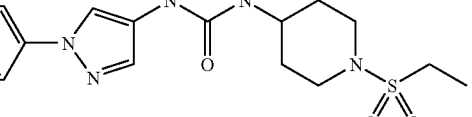<br>Y5 Ki = 1.2 nM | (CDCl$_3$) δ 8.31 (s, 1H),<br>7.60 (s, 1H), 7.22 (m, 2H),<br>6.68 (m, 1H), 6.47 (s, 1H),<br>5.78 (s, br, 1H), 4.55 (m, 1H),<br>4.38 (s, br, 1H), 3.12 (s, br, 1H),<br>2.86 (s, 3H), 2.65 (s, br, 1H),<br>2.90–1.50 (m, 5H), 0.98 (m, 2H),<br>0.77 (m, 2H). | 404 |
| 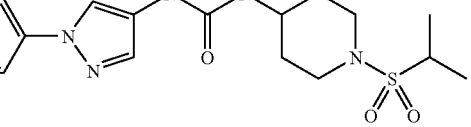<br>Y5 Ki = 0.70 nM | (CDCl$_3$) δ 8.31 (s, 1H),<br>7.60 (s, 1H), 7.22 (m, 2H),<br>6.68 (m, 1H), 6.48 (s, 1H),<br>4.90 (d, br, 1H),<br>4.52 (m, 1H), 4.05 (d, br, 1H),<br>3.15 (t, 1H), 2.86 (s, 3H),<br>2.82 (m, 1H), 2.62 (t, 1H),<br>1.90–1.50 (m, 4H), 1.13 (m, 6H). | 406 |
| 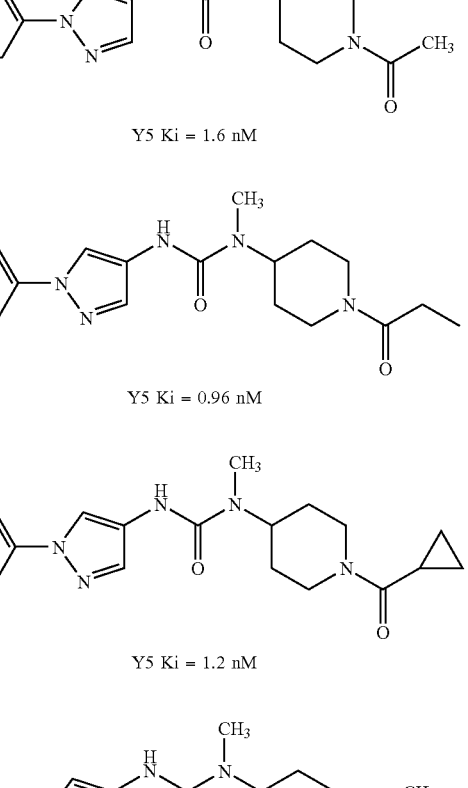<br>Y5 Ki = 0.89 nM | (CDCl$_3$) δ 8.29 (s, 1H), 7.61 (s, 1H),<br>7.22 (m, 2H), 6.68 (m, 1H),<br>6.48 (s, 1H), 4.45 (m, 1H),<br>3.95 (d, br, 2H), 3.02–2.85 (m, 7H),<br>1.77 (m, 4H), 1.36 (t, 3H). | 428 |
| 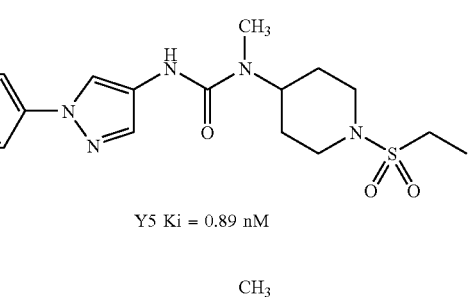<br>Y5 Ki = 1.7 nM | (CDCl$_3$) δ 8.27 (s, 1H),<br>7.63 (s, 1H), 7.22 (m, 2H),<br>6.68 (m, 1H), 6.55 (s, 1H), 4.43<br>(m, 1H), 4.95 (d, br, 2H),<br>3.19 (m, 1H), 2.98 (m, 2H),<br>2.86 (s, 3H), 1.72 (m, 4H),<br>1.33 (m, 6H). | 442 |

Experiment 1. Synthesis of

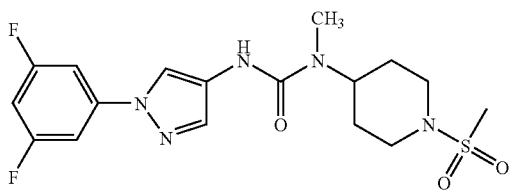

Step 1. Synthesis of 1:

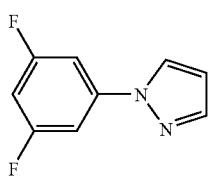

Pyrazole (5.00 g, 73.4 mmol), 3,5-difluorophenyl boronic acid (11.60 g, 73.4 mmol), anhydrous Cu(OAc)$_2$ (13.33 g, 73.4 mmol), anhydrous pyridine (12.0 ml, 146.8 mmol) and anhydrous methylene chloride (30 ml) were added to a round bottom flask to form a mixture. The mixture was stirred at room temperature for 2.5 days, afterwards cold water (~200 ml) was added. The mixture was extracted with methylene chloride (3×200 ml) and dried over Na$_2$SO$_4$. The concentrated residue was separated by flash column chromatography (hexane:EtOAc=100:0→6:1, v/v) to afford 1 (2.90 g, 22%) as yellowish solid. $^1$HNMR (CDCl$_3$) δ 7.89 (m, 1H), 7.73 (d, 1H), 7.27 (m, 2H), 6.73 (m, 1H), 6.50 (m, 1H). MS m/e 181 (M+H)$^+$.

Step 2. Synthesis of 2:

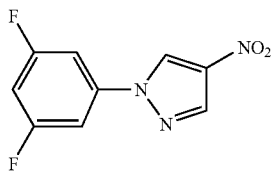

Compound 1 (2.90 g, 16.1 mmol) and acetic anhydride (10.0 ml) were added to a round bottom flask to form a mixture. The mixture was cooled to 0° C. Next, fuming nitric acid (1.2 ml) in acetic anhydride (5.0 ml) was added slowly. The reaction mixture was warmed up to room temperature and stirred for 5 hours and additional fuming nitric acid (1.2 ml) in acetic anhydride (5.0 ml) was added. The mixture was stirred for additional 17 hours and poured into sat. NaHCO$_3$ (~50 ml) and extracted with CH$_2$Cl$_2$ (3×100 ml). The organic layer was subsequently dried over Na$_2$SO$_4$, filtered and concentrated to provide 2 (3.10 g, 86%) that was used without further purification. $^1$HNMR (CDCl$_3$) δ 8.62 (s, 1H), 8.27 (s, 1H), 7.32 (m, 2H), 6.89 (m, 1H).

Step 3. Synthesis of 3:

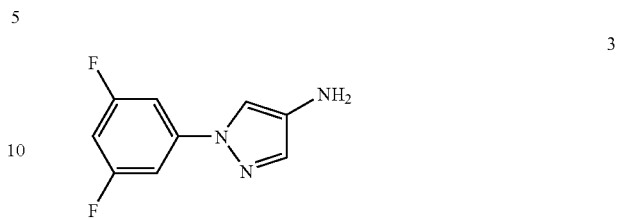

Compound 2 (3.10 g, 13.8 mmol), 10% Pd/C (0.6 g) and methanol (100 ml) were added to a round bottom flask to form a mixture. This mixture was stirred at room temperature under a hydrogen balloon overnight. The mixture was then filtered through celite and concentrated. The residue was separated by flash column chromatography (Hexane→3% EtOAc/Hexane, v/v) to give 3 (2.10 g, 78%) as light brown solid. $^1$HNMR (CDCl$_3$) δ 7.44 (s, 1H), 7.39 (s, 1H), 7.16 (m, 2H), 6.65 (m, 1H). MS m/e 196 (M+H)$^+$.

Step 4. Synthesis of 4

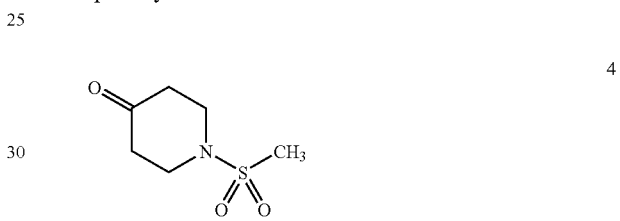

4-Piperidone hydrate hydrochloride (40.00 g, 0.260 mol) and THF (320 ml) were added to a round bottom flask to form a solution. This solution was stirred at room temperature, to which CH$_3$SO$_2$Cl (31.0 ml, 0.402 mol) and 15% aq. NaOH (156 ml) were added very slowly to keep temperature 26–32° C. After this addition, the reaction mixture was stirred at room temperature for 2 hours, then transferred to a separation funnel. The organic layer was collected and the aqueous layer was extracted with THF (2×250 ml). The combined organic layer was dried over Na$_2$SO$_4$. After filtration, the concentrated residue was washed with hexane to give 4 (46.00 g, 99.7%) as white solid $^1$H NMR (CDCl$_3$) δ 3.59 (t, J=6.00 Hz, 4H), 2.89 (s, 3H), 2.59 (t, J=5.6 Hz, 4H).

Step 5. Synthesis of 5

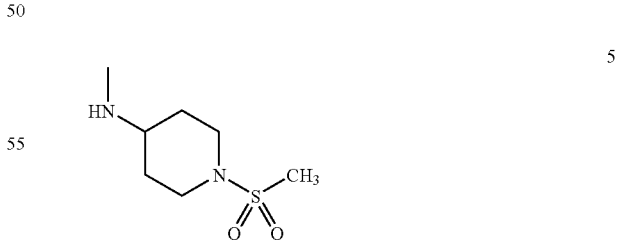

Compound 4 (40.00 g, 0.226 mol), CH$_3$CN (240 ml), 40% CH$_3$NH$_2$ (20.4 ml, 0.263 mol) were added to a round bottom flask. The reaction mixture was stirred at room temperature for 1 hour. To another round bottom flask, NaBH(OAc)$_3$ (60.00 g, 0.283 mol) and 120 ml of CH$_3$CN were added. This solution was stirred at −10° C., to which the above solution was added very slowly via an additional funnel.

After the addition, the reaction was allowed to warm to room temperature and stirred overnight. The reaction mixture was concentrated to a small volume, to which 1N aq. NaOH (282 ml) was added. This resulting solution was extracted with CH$_2$Cl$_2$ (3×500 ml) followed by extraction with toluene until no product remained in the extraction solution. The combined organic layer was dried over Na$_2$SO$_4$. After filtration, the solution was concentrated in vacuo to give 5 (29.00 g, 62.9%) as white solid. $^1$H NMR (CDCl$_3$) δ 3.66 (m, 2H), 2.84 (m, 2H), 2.76 (s, 3H), 2.52 (m, 1H), 2.42 (s 1.96 (m, 2H), 1.45 (m, 2H). MS m/e 193 (M+H)$^+$ Step 6. Synthesis:

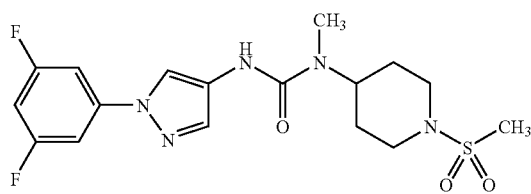

Compound 3 (100 mg, 0.513 mmol) and anhydrous pyridine (2 ml) were added to a round bottom flask to form a mixture. This mixture was stirred at room temperature under argon. Phenyl chloroformate (96 mg, 0.615 mmol) was slowly added to this mixture. The mixture was subsequently stirred at room temperature overnight and evaporated. The resulting residue was used directly in the next step without further purification.

The residue from the above step was dissolved in chloroform (4 ml). Subsequently, compound 5 (118 mg, 0.614 mmol) and Et$_3$N (156 mg, 1.54 mmol) were added. This reaction mixture was refluxed overnight, allowed to cool to room temperature and poured into water. The solution was then extracted with methylene chloride (3×20 ml) and dried over sodium sulfate. The concentrated residue was separated by preparative TLC (MeOH:CH$_2$Cl$_2$=1:20, v/v) to afford the product (150 mg, 71%) as a pale solid.

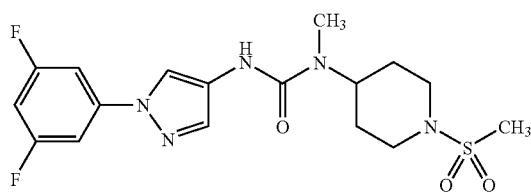

Experiment 2. Synthesis of

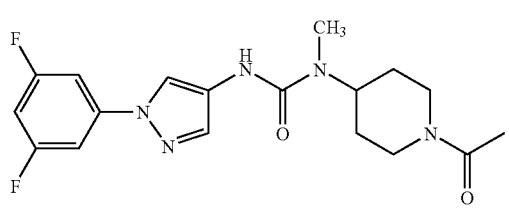

Step 1. Synthesis of 6:

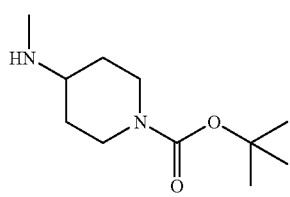

Compound 6 was synthesized from tert-butyl 4-oxo-1-piperidinecarboxylate and methylamine using the same procedure of Experiment 1, Step 5.

Step 2. Synthesis of:

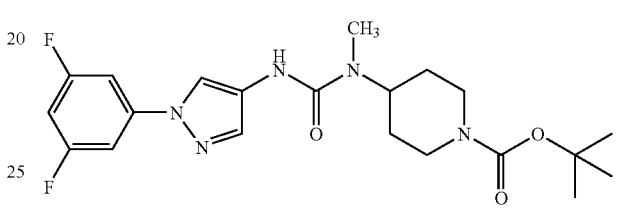

The above compound, was synthesized from 3 and 6 using same procedure of Experiment 1, Step 6.

Step 3. Synthesis of:

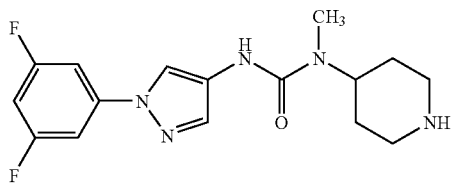

The above compound (1.85 g, 4.25 mmol) and 4M HCl/1,4-dioxane (30 ml) were added to round bottom flask to form a mixture. The mixture was stirred at room temperature for 5 hours and concentrated in vacuo to afford the product as a hydrochloride salt in quantitative yield.

Step 4. Synthesis of:

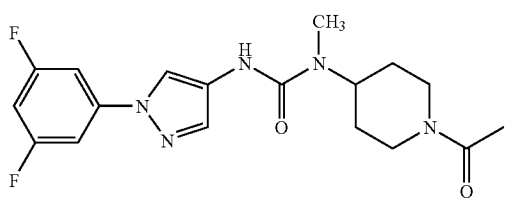

The above compound (50.0 mg, 0.134 mmol), triethylamine (45.3 mg, 0.448 mmol) and anhydrous methylene chloride (2 ml) were added to a round bottom flask to form a mixture. This mixture was stirred at room temperature. Acetic anhydride (15.0 mg, 0.146 mmol) was added. The mixture was subsequently stirred at room temperature overnight and separated by preparative TLC (MeOH:CH$_2$Cl$_2$=1:20, v/v) directly to afford the following compound (48.4 mg, 96% yield) as a white solid.

The compounds below were synthesized by using the same procedure described above.

What is claimed is:

1. A compound represented by the structural formula I or a pharmaceutically acceptable salt or solvate, wherein:
m is 2;
n is 2;
$R^1$ is 0 to 5 substituents which can be the same or different, each being independently, —OH, halogen, alkyl, haloalkyl, cycloalkyl, —CN, alkoxy, cycloalkoxy, alkylthio-, cycloalkylthio-, —NR$^5$R$^6$, —NO$_2$, —C(O)NR$^5$R$^6$, —NR$^5$C(O)R$^6$, —NR$^5$C(O)NR$^5$R$^6$ where the two R$^5$ moieties can be the same or different, —NC(O)OR$^7$, —C(O)OR$^5$, —SOR$^5$, —SO$_2$R$^5$, —SO$_2$NR$^5$R$^6$, aryl or heteroaryl;
$R^2$ is 0 to 2 subsituents which can be the same or different, each being independently, —OH, halogen, alkyl, haloalkyl, cycloalkyl, —CN, alkoxy, cycloalkoxy, alkylthio-, cycloalkylthio-, —NR$^5$R$^6$, —NO$_2$, —C(O)NR$^5$R$^6$, —NR$^5$C(O)R$^6$, —NR$^5$C(O)NR$^5$R$^6$ where the two R$^5$ moieties can be the same or different, —NC(O)OR$^7$, —C(O)OR$^5$, —SOR$^5$, —SO$_2$R$^5$, —SO$_2$NR$^5$R$^6$, aryl or heteroaryl;
$R^3$ is hydrogen or alkyl;
$R^4$ is 0 to 6 substituents which can be the same or different, each being independently alkyl, alkoxy, haloalkyl or —OH;
$R^5$ and $R^6$ can be the same or different each being independently hydrogen, alkyl, aryl, heteroaryl, aralkyl, heteroaralkyl, haloalkyl or cycloalkyl;
$R^7$ is alkyl or cycloalkyl;
Z is NR$^8$ or;
$R^8$ is hydrogen, —SO$_2$R$^{10}$, —SO$_2$NR$^5$R$^{11}$, —C(O)R$^{11}$, —C(O)NR$^5$R$^{11}$ or —C(O)OR$^{10}$;
$R^{10}$ is alkyl, cycloalkyl, aryl or heteroaryl; and
$R^{11}$ is hydrogen, alkyl, cycloalkyl, aryl or heteroaryl.

2. The compound of claim 1 having formula II:

formula II or a pharmaceutically acceptable salt or solvate thereof, wherein:
$R^1$ is 2 substituents which are halogens that can be the same or different;
$R^3$ is alkyl;
and
R is —SO$_2$R$^{10}$ or —C(O)R$^{11}$.

3. The compound of claim 1 wherein $R^1$ is a halogen.
4. The compound of claim 3 wherein $R^1$ is 2 substituents.
5. The compound of claim 4 wherein each $R^1$ is fluorine.
6. The compound of claim 1 wherein $R^2$ is 2 substituents.
7. The compound of claim 6 wherein each $R^2$ is hydrogen.
8. The compound of claim 1 wherein $R^3$ is alkyl.
9. The compound of claim 8 wherein $R^3$ is methyl.
10. The compound of claim 1 wherein $R^4$ is hydrogen.
11. The compound of claim 1 wherein $R^8$ is —SO$_2$CH$_3$, —C(O)OC(CH$_3$)$_3$, hydrogen, —C(O)CH$_3$, —C(O)CH$_2$CH$_3$, —C(O)cyclopropyl, —C(O)CH(CH$_3$)$_2$, —SO$_2$CH$_2$CH$_3$ or —SO$_2$CH(CH$_3$)$_2$.

12. A compound selected from the group consisting of

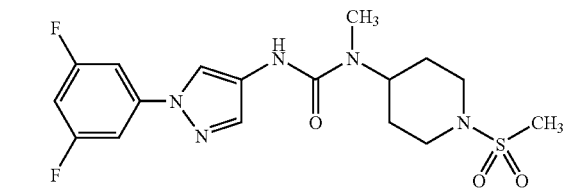
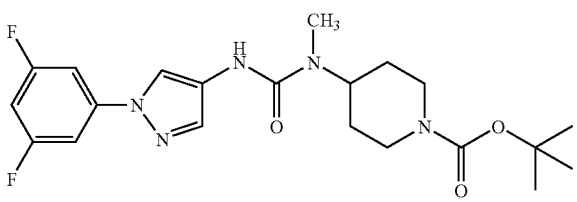
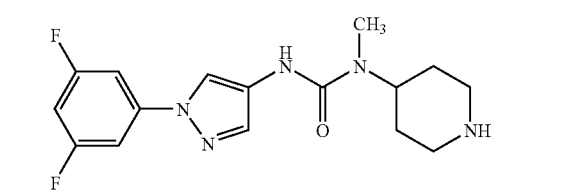
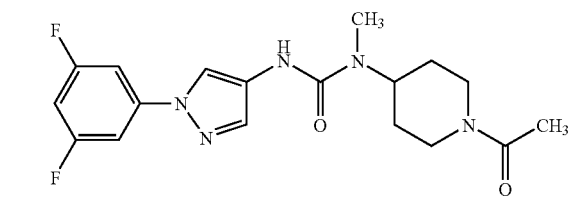
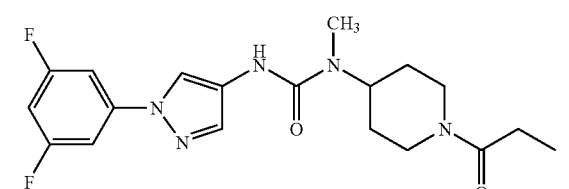
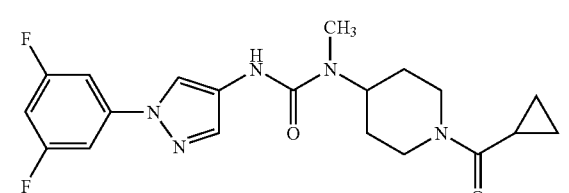

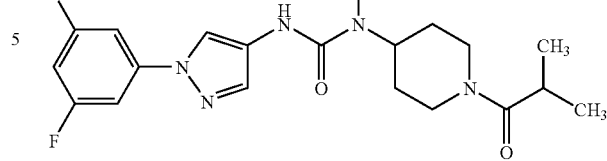

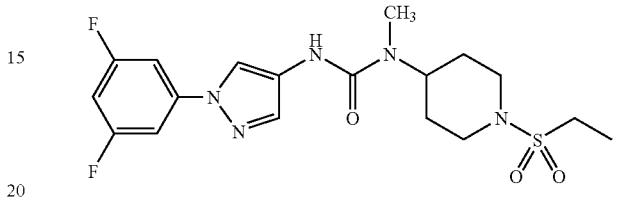

and

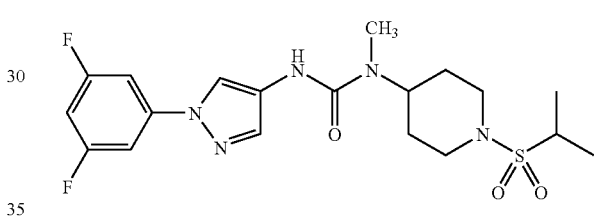

or a pharmaceutically acceptable salt or solvate.

13. A pharmaceutical composition comprising a therapeutically effective amount of at least one compound of claim 1 in combination with at least one pharmaceutically acceptable carrier.

14. A pharmaceutical composition comprising a therapeutically effective amount of at least one compound of claim 12 in combination with at least one pharmaceutically acceptable carrier.

15. A process for making a pharmaceutical composition comprising combining at least one compound of claim 12, and at least one pharmaceutically acceptable carrier.

* * * * *

UNITED STATES PATENT AND TRADEMARK OFFICE
CERTIFICATE OF CORRECTION

PATENT NO. : 7,157,472 B2  
APPLICATION NO. : 10/609638  
DATED : January 2, 2007  
INVENTOR(S) : Andrew Stamford et al.

Page 1 of 1

It is certified that error appears in the above-identified patent and that said Letters Patent is hereby corrected as shown below:

In the Claims:

Claim 2, col. 26, line 54: Please correct "R is" to --R8 is--.

Signed and Sealed this

Fourth Day of March, 2008

JON W. DUDAS  
*Director of the United States Patent and Trademark Office*